(12) United States Patent
Gupta et al.

(10) Patent No.: US 6,746,890 B2
(45) Date of Patent: Jun. 8, 2004

(54) THREE DIMENSIONAL THIN FILM DEVICES AND METHODS OF FABRICATION

(75) Inventors: Vikas Gupta, San Leandro, CA (US); A. David Johnson, San Leandro, CA (US); Letecia Menchaca, Berkeley, CA (US); Valery Martynov, San Francisco, CA (US)

(73) Assignee: TiNi Alloy Company, San Leandro, CA (US)

(*) Notice: Subject to any disclaimer, the term of this patent is extended or adjusted under 35 U.S.C. 154(b) by 30 days.

(21) Appl. No.: 10/198,654

(22) Filed: Jul. 17, 2002

(65) Prior Publication Data

US 2004/0014253 A1 Jan. 22, 2004

(51) Int. Cl.[7] ............................................. H01L 21/00
(52) U.S. Cl. .............................. 438/50; 438/51; 438/52; 438/53
(58) Field of Search ......................... 438/50, 51, 52, 438/53, 455–459

(56) References Cited

U.S. PATENT DOCUMENTS

| | | | | |
|---|---|---|---|---|
| 5,543,349 A | * | 8/1996 | Kurtz et al. ................... | 437/60 |
| 5,714,690 A | * | 2/1998 | Burns et al. ................... | 73/721 |
| 5,840,199 A | * | 11/1998 | Warren ........................... | 216/2 |
| 5,930,651 A | * | 7/1999 | Terasawa ........................ | 438/456 |
| 6,410,360 B1 | * | 6/2002 | Steenberge .................... | 438/52 |
| 6,451,668 B1 | * | 9/2002 | Neumeier et al. ........... | 438/401 |
| 6,537,310 B1 | | 3/2003 | Palmaz et al. ............... | 623/1.13 |
| 2002/0081821 A1 | * | 6/2002 | Cabuz et al. ................. | 438/455 |

* cited by examiner

Primary Examiner—Alexander Ghyka
(74) Attorney, Agent, or Firm—Richard E. Backus

(57) ABSTRACT

Methods for making thin film multiple layered three-dimensional devices using two-dimensional MEMS techniques for use in a variety of applications including endovascular, endolumenal, intracranial, and intraocular medical applications. In the general method, a thin film first layer of the device material is deposited over a release layer which in turn is deposited on a substrate. An other release layer is deposited on the first device layer, with portions of the other release layer removed, leaving a pattern in the first device layer. In a similar manner a second layer of device material is formed in a pattern overlying the first device layer with portions of the two layers joined together leaving a portion of the release layer between them. The two release layers are removed and the first and second layers of the device material are formed into a three-dimensional shape suitable for the desired end-use application.

21 Claims, 13 Drawing Sheets

THREE DIMENSIONAL THIN FILM DEVICES AND METHODS OF FABRICATION

BACKGROUND OF THE INVENTION

1. Field of the Invention

This invention relates to methods for manufacturing devices of three-dimensional shapes using two-dimensional micro-electro-mechanical system (MEMS) techniques. The invention can be applied to materials with or without shape memory or superelastic properties, and has widespread applications, especially for fields and industries that have a demand for a high degree of miniaturization of devices and equipment.

2. Description of the Related Art

In recent years many medical devices have been introduced that incorporate shape memory and superelastic materials, especially titanium nickel alloys often referred to as TiNi or Nitinol. Two principal products are guidewires for catheters and stents used in the treatment of vascular disease. Use of Nitinol in stents fabricated from small diameter Nitinol tubing has grown rapidly.

Fabrication of stents includes the operations of laser cutting, expansion, heat treatment, and electropolishing. These processes are labor intensive and costly. Stents made from tubing are generally lacking in flexibility required to treat small blood vessels in the brain that must be accessed intralumenally through tortuous distal paths in the carotid artery.

Accordingly there is a need for improved devices to be used in the intracranial vasculature. The present invention provides an alternative method of fabricating tools for endolumenal use that result in devices that are small, flexible, inexpensive to make, smooth-surfaced, chemically resistant, and possess superelastic and shape memory properties. These devices include stents, filters, blood clot retrievers, aneurysm closures, and anastomosis devices for use in conjunction with blood vessel transplants.

Thin TiNi film has desirable characteristics for fabricating these devices, especially because it can be rolled, folded, or otherwise compressed for insertion through micro-catheters.

Production of complete systems for minimally invasive vascular treatment involves joining of components by welding, brazing, soldering, and adhesives. Superior performance can be achieved if the number of such attachments is minimized. Additionally, welding of thin film (micrometers thick) presents novel problems. It is desirable to make the device all in one piece to achieve maximum flexibility, strength, and minimal thrombo-genicity.

The most common method of producing thin metal films is by vacuum sputtering, generally onto a planar substrate. Sputtering onto three-dimensional substrates can be accomplished by rotation of the substrate in or near the plasma, and by cylindrical sputtering. While it has been shown that it is possible to sputter three-dimensional shapes, it is also known that the material thus produced by this method is not of the highest quality, and the methods do not lend themselves to production of large numbers of devices at low cost.

In cylindrical sputtering it is difficult to achieve the correct chemical composition. For intravascular use, the transition temperature should be below body temperature, 36.6° C., to take advantage of superelasticity.

In three-dimensional deposition it is difficult to achieve good crystal structure of the deposited thin film alloy. This requires shielding to produce line-of-sight normal deposition, otherwise columnar structure appears with poor intra-crystalline and inter-crystalline adhesion. Brittleness results.

It is also difficult to remove the three-dimensional structure from the substrate. Etchants must be extremely selective, and must not interact with the thin film material, generally TiNi or TiNi-based.

Miniature devices made of free-standing thin film shape memory alloys such as Nitinol have potential applications in medicine, particularly in minimally invasive surgery of the vasculature. For a majority of endolumenal applications it is essential that these devices have three-dimensional shapes, i.e. cones, cylinders, and hemispheres, to take advantage of superelastic and shape memory properties. In applications relating to tissue engineering, these three-dimensional shapes of Nitinol thin film can be used as a base structural material or scaffold on which to grow artificial tissue cells. For example, tissue grown on a thin film cylinder will produce an artificial blood vessel in a tubular shape.

The most practical method of creating thin films of shape memory alloy is by vacuum sputtering. Sputtering onto three-dimensional substrates is wasteful, slow, and subject to difficulties not encountered in planar deposition.

The need has therefore been recognized for medical device fabrication methods which obviate the foregoing and other limitations and disadvantages of prior art fabrication methods and devices of the type described. Despite the various fabrication methods and devices in the prior art, there has heretofore not been provided a suitable and attractive solution to these problems.

OBJECTS AND SUMMARY OF THE INVENTION

It is a general object of the invention to provide methods of manufacturing devices of three-dimensional shapes using two-dimensional micro-electro-mechanical techniques.

Another object is to provide methods to make multiple layered three-dimensional shapes with pockets created selectively between the layers, such as for endovascular, endolumenal, intracranial, and intraocular medical applications.

Another object is to provide devices made by methods of the type described.

The prior art limitations and limitations described above are overcome in the present invention by methods that comprise planar material deposition that has advantages including high deposition rates, improved control of composition, and use of large substrates to make batches of devices rather than individual devices. This leads to a practical manufacturing method for large volume production.

The methods of the invention comprise the removal of material by chemical means that, combined with planar sputter deposition of multiple layers, photolithography, and heat treatment, enables the fabrication of hollow shapes having thin film surfaces of sufficiently small size for use in medicine, including endovascular, endolumenal, intracranial, and intraocular applications.

DESCRIPTION OF THE PREFERRED EMBODIMENTS

Figure 1:
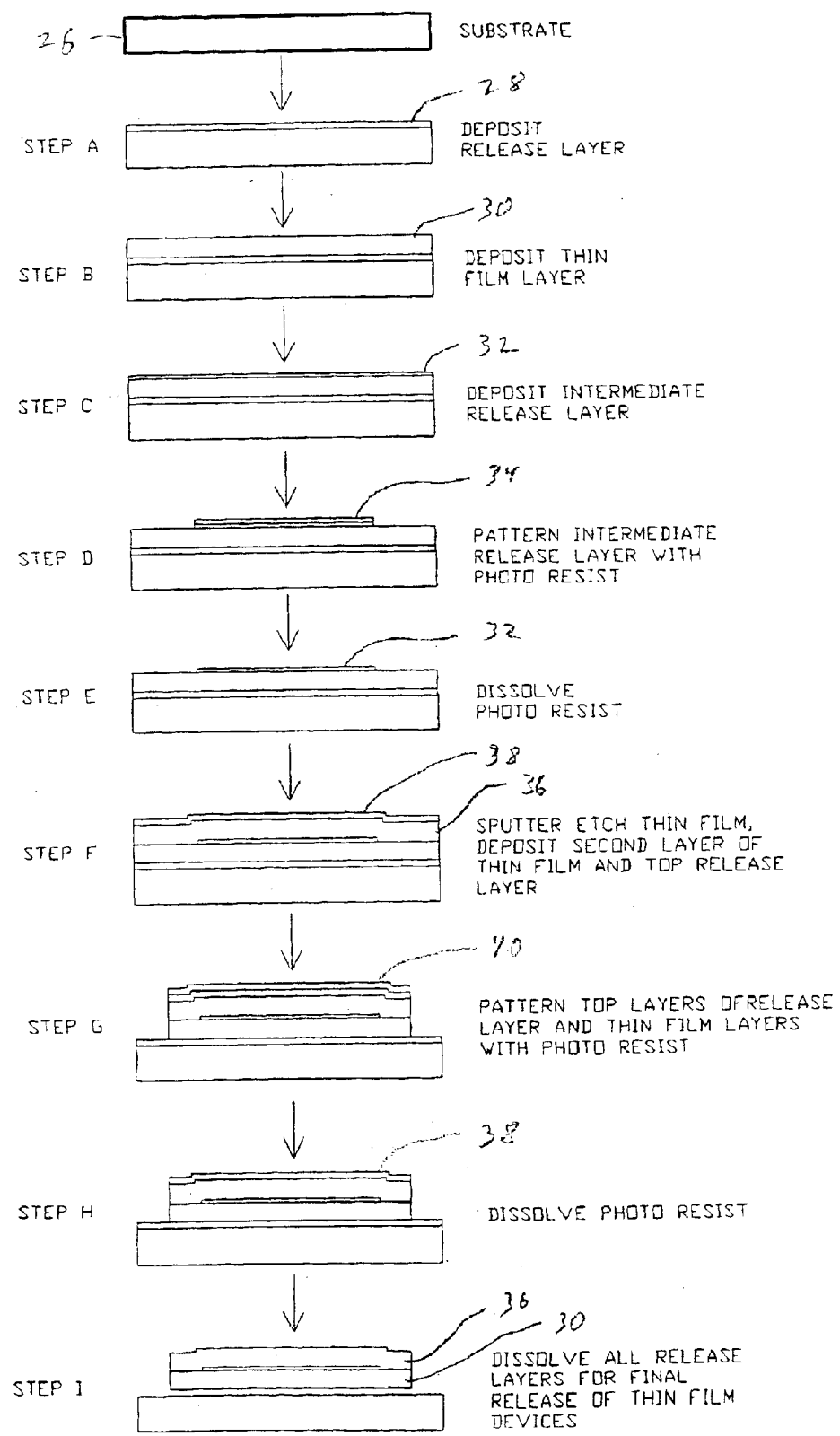
FIG. 1 is a block diagram showing the general steps in the method of one embodiment of the invention.

In a broad aspect of the invention, three-dimensional shapes, especially cones, cylinders and hemispheres, are made by methods which comprise opening two-dimensional, multiple-layered planar structures of micrometer (mm) size. This enables the design and development of shape memory thin film actuated micro-apparatus as therapeutic devices for the medical industry. One such example is the development of an endovascular apparatus for the treatment of intracranial aneurysms. The methods of the invention will also enable the design of medical endolumenal implants for various endovascular as well as other medical applications. In most of these methods, the principle functional materials used are thin film TiNi (also termed NITINOL) which is an alloy of nearly equal atomic compositions of titanium and nickel, or its derivatives such as CuAlNi or TiNiPd alloys. These shape memory alloys (also termed SMA) have the properties of shape memory effect and superelasticity. The superelastic properties of SMA are discussed in the publication: K. Otsuka, C. M. Wayman, eds. Shape Memory Materials, Cambridge University Press 1998 at pages 27 et. seq.

The SMA material is annealed into a crystalline state so that it undergoes a crystalline phase transformation from martensite to austenite when heated through the material's phase change transformation temperature. When below that temperature the material can be plastically deformed from its memory shape in response to a stress. When the deformed SMA material is heated through the transformation temperature, it forcefully reverts to its memory shape while exerting considerable force. The transformation temperature of TiNi having equal atomic compositions of the two elements can be made in the range of about 50 to 70° C., and suitable adjustments of the alloy compositions can achieve transformation temperatures ranging from 0° C. to 100° C. During the alloying process, a third metal such as hafnium or palladium can be amalgamated with the Ti and Ni elements to raise the transition temperature, while iron or vanadium can be amalgamated with the Ti and Ni to lower the transition temperature, as required for particular applications.

When the SMA composition of a three-dimensional shape is made such that the transformation temperature is below the 36.6° C. (normal temperature of the human body) then the SMA becomes superelastic when heated by blood temperature through the transformation temperature. As a superelastic, the device while in its high temperature phase can be stressed to deform as much as from 3 to 5% without being damaged. This superelasticity enables the device to deform enough for insertion through endolumenal structures of the body, such as being folded under compression within a microcatheter. The stress is removed by withdrawing the device from the microcatheter, allowing it to recover its shape.

Thin film devices may be fabricated by using microfabrication techniques involving sputtering of metals and TiNi alloys. Typically these thin layers of metal and metal alloys are sputtered using DC magnetron and RF sputtering techniques. The planar thin film structures are built up layer-by-layer through sputter deposition. Alternating layers of TiNi and sacrificial material are sputtered on a smooth flat surface of a substrate, for example a silicon wafer. TiNi and the sacrificial material layers are selectively patterned by micro-photolithography techniques in which a thin layer of photo resist material is spin-coated and used to selectively remove the material to form a pattern on these layers.

Appropriate designs, to construct various shapes, are printed on photo masks which are eventually used for creating the desired patterns on the TiNi and sacrificial material layers. These multi-layered thin film structures are heat treated at temperature of 500° C. in order to crystallize sputtered TiNi material. TiNi, after annealing, exhibits the desired shape memory and superelastic properties. These planar multi-layered thin film structures are transformed into various three-dimensional shapes by insertion of shape forming mandrels and heat-treatment.

For various applications, three-dimensional shapes of thin film are required to have certain fenestration patterns. As used herein, the term thin film means a film with of thickness less than 50 microns. Fenestrations patterns are generated on these devices in their planar form using micro-photolithography techniques. Since these fenestration patterns are generated photochemically, the sizes and shapes of these patterns can be controlled very precisely and uniformly. The diameters of the fenestrations are sufficient to allow blood cells to pass by which block larger size clots, and can be in the range of 30 mm to 40 mm. Very sharp and well defined edge quality is thereby achieved. These micron-scaled fenestration patterns are generated on thin film by spin coating a thin layer of photo resist which is then patterned using a photomask glass plate containing the fenestration patterns in the form of clear and opaque regions. This allows the etching of thin films, both TiNi and sacrificial layers, from the selective regions. Appropriate etching solutions are used in order to etch different metal layers, selectively, without damaging the other metal layer. After generating the final fenestration patterns and final device features, the multi-layered thin film devices are released from the substrate by chemically dissolving the sacrificial layers away.

The methods of the invention for forming three-dimensional shapes of thin film can be extended from two layers to any number of thin film layers. Various ingenious features are generated and added on to a three dimensional shape by sputtering more than two layers of thin film material. Pockets between two layers on a three-dimensional surface are by sputtering multiple layers of thin film material by selectively etching a sacrificial layer. The pockets between the two thin film layers in the final device are used for insertion or attachment of outside structures such as a catheter or wire to the three-dimensional thin film devices.

The methods of the invention for forming three-dimensional shapes of thin film can also be extended to create different fenestration patterns in each layer of thin film.

Among the three-dimensional thin film shapes and their possible use for medical applications are the following. Fenestrated cone shapes are intended to be used for retrieval of blood clots, particularly clots causing ischemic stroke. Cylinder shapes are intended for use as stents to support blood vessels from collapse and stenosis, and to permit treatment of intracranial aneurysms. Cylindrical shapes are also intended for use as a scaffold structure for making artificially grown blood vessels of all sizes. Hemispherical shaped structures are for insertion into aneurysms to isolate them from blood flow in parent blood vessels. Dome-shaped structures having multiple layers of thin film are intended to be used in intraocular devices for lens implantation. Pockets and channels formed between the two thin film layers enable the attachment of a lens onto a dome-like thin film structure for use in ocular applications.

Cones or cylinders which are formed from more than two layers of thin film to create channels (or pockets) between the two layers allow the insertion of an outer structure into the thin film structure. In the context of blood clot retrieval devices, a set of such pockets are used as means for attaching wires or other external parts of a catheter to the thin film cone and cylinders.

Multiple-part devices of the type described are used for osculature of blood vessels. A short segment of fenestrated cylinder is inserted into each end of a pair of blood vessels to be joined, in such a way that they exert an outward pressure on the blood vessel lumen tending to keep it open and to return it to an open shape when crushed. A third cylinder, having a larger diameter, is then placed over the ends. This member will exert an inward pressure. The result is an anastomosis of the two blood vessel ends, in which the blood vessel wall is gently pressed between the two inner cylinders and the outer cylinder. The outer cylinder will be stretched so that when it is placed it gently forces the two ends of the blood vessel against each other to form a seal and to promote healing.

Deploying or implanting medical devices using micro-catheters through tortuous small blood vessels, in the brain for example, requires devices that are extremely flexible and miniaturized. Such flexible and miniaturized devices are made by the thin film deposition methods of the invention creating extremely thin films with thickness less than 50 mm. Although thin film can be fabricated using several deposition techniques, sputter deposition techniques are mainly used for fabricating thin film stents.

In the invention, thin film sputtering methods involve three basic steps: 1) generation of the atomic or ionic species from the metal or alloy material target, 2) transport of these species from the target to a substrate through a gas or a plasma medium, and 3) condensation of these species on the substrate surface to form a solid thin film. In the context of this invention, the target can be of any metal or metal alloys, the substrate can be a polished silicon or glass wafer and argon gas can be used to generate an intense plasma.

To form the devices, thin film is sputtered in a process chamber which contains the target material and a rotating table to mount the substrates. In the invention, since the devices are fabricated using a multi-layered thin film system, the process chamber is capable of accommodating multiple sputtering targets. The chamber allows sputtering from one or all the targets in both RF and DC sputtering mode. In the process chamber, vacuum in the range of low $10^{-7}$ torr is accomplished by the help of one or more vacuum pumps such as a mechanical pump, cryo pump or turbo molecular pump. Argon gas (or other inert gas) at a low pressure (around few millitorr) is introduced into the chamber. Upon applying a high voltage to the target material from a DC or an RF power supply, a glow discharge is created which dissociates the argon atoms into an intense cloud of ions called plasma. These ions in the plasma are accelerated to the target material and are capable of dislodging atoms from the target surface. These dislodged atoms condense on the substrate surface which is mounted on the table, thereby depositing thin film on the substrate.

FIG. 1 shows the principal steps in the method of fabricating two-layered thin film devices without forming any fenestration patterns. Multiple layers of thin film device material and sacrificial material are sputter deposited sequentially on a surface of substrate 26, which is an oxidized silicon wafer, in the process chamber. Device material can be TiNi, other derivative alloys of TiNi, stainless steel, and the like. Shape memory alloys such as TiNi can be sputter deposited, but they cannot be deposited by electroplating. Many non-SMA alloys and metal can be deposited by electroplating to form portions of the devices. Sacrificial material can be chromium, aluminum, copper, TiCuAg or any other metal or alloy. To create such multiple layers, the process chamber is equipped with two separate targets: one for the thin film device layer and the other for the sacrificial layer. Preferably the device layer is deposited using DC sputtering and the sacrificial layer using RF sputtering. Sputtered thin film alloy can also be achieved by either sputtering from a single alloy target or by co-sputtering from multiple targets. Polished and oxidized silicon wafers are used as substrates and are loaded into the chamber which is pumped down to achieve vacuum in a low $10^{-7}$ torr range. Highly polished and flat glass wafer can also be used as the substrate.

As shown in FIG. 1, a thin release or sacrificial layer 28 is sputter deposited on the substrate using RF sputtering at argon pressure of about 2 millitorr (FIG. 1, step A). Thickness of the deposited thin film 28 can be 500 Å or more. A thin device layer 30 of the device material is sputter deposited on top of the sacrificial layer using DC sputtering at an argon pressure of about 2 millitorr (FIG. 1, step B). Thickness of the deposited device layer 30 can be from 1 mm to 50 mm. A thin sacrificial layer 32 is then sputter deposited on top of the device layer (FIG. 1, step C). Typical thickness of this layer 32 is about 100 Å. This layer plays two roles: 1) it acts as a protective layer for the underlying device layer during subsequent lithography steps, and 2) it acts as a sacrificial layer which in the final steps of fabrication is dissolved away chemically in order to selectively create a pocket between the two device layers.

For making three-dimensional thin film shapes as shown in FIGS. 5 to 10, two suitable photo masks (mask A and mask B, both not shown) with appropriate pattern designs are required. A photo mask is typically a high quality chrome coated glass plate with desired device patterns etched on to the chrome layer which finally results in opaque and clear regions correspondingly on the mask plate. Designs on the mask determine the final three-dimensional shape of the device. For example, solid triangular designs for cones, rectangular for cylinders, semicircular for hemispheres, etc. Mask B contains designs for final definition of the device, fenestration patterns or any other surface pattern which may be needed for the final device. Mask A is used to pattern the top sacrificial layer deposited on the wafer described above.

To pattern the above sputtered wafer with designs on mask A, typical steps of micro-photolithography technique are followed. A thin layer 34 of positive photo resist liquid is spin-coated on the above wafer at about 4000 rpm and baked at 90° C. in a clean room convection oven. Using an ultraviolet light mask aligner, the wafer and mask A are aligned and the photo resist layer is UV exposed though the mask plate which transfers the patterns from mask A on to the photo resist layer. The wafer with exposed photo resist is immersed in developer solution to selectively remove the exposed sections of the photo resist thus creating windows in the photo resist layer on the wafer. When immersed in a chemical etchant, these windows in the photo resist allow for the selective etching of the sacrificial layer as shown in FIG. 1, step D. After patterning the sacrificial layer, the photo resist layer is chemically dissolved away by immersing in a solvent (FIG. 1, step E) which also concludes the photolithography process.

The wafer with the selectively etched sacrificial layer is loaded back into the sputtering chamber which is then pumped down to low $10^{-7}$ torr vacuum. In the chamber, the top exposed surface layer is sputter-etched to clean it from any contamination. Sputter-etch is a process similar to sputtering except that in the case of sputter-etch the argon ions are accelerated to the substrate surface rather than the target surface. High energetic argon ions when operated in sputter-etch mode also remove undesired thin native oxide layer on the surface which may have formed during the lithography process. Followed by the sputter-etch, another device layer 36 of device material and a sacrificial layer 38 are sputter deposited on the substrate (FIG. 1, step F). The thickness of these layers may remain the same as in steps B and C.

Where the sputtered device material is TiNi or any other shape memory alloy, the material is heat-treated at 500° C.

in vacuum for crystallization so that the material exhibits the properties of shape memory alloy and superelasticity. To achieve this, the sputtered wafer from above is mounted on a hot plate which is situated in a vacuum chamber. In a reasonable vacuum, the power to the hot plate is turned on and the temperature is monitored at the bottom and top end of the wafer using thermocouples.

As illustrated in FIG. 1, step G, the layer 40 of photo resist is spin-coated to pattern the layers with designs in mask B using the photolithography steps described herein. In this step, after etching the top sacrificial layer 38, the underlying device layers are also chemically etched with the same mask design in order to define the device's outer features. This is followed by the complete removal of photo resist layer 40 (FIG. 1, step H). To separate the devices from the surface of the substrate, the whole wafer with patterned layers is immersed into the chemical etchant to completely dissolve the sacrificial layer (FIG. 1, step I), leaving the patterned device layers 30 and 36. The etchant for this purpose should be such that it should etch the sacrificial material selective to the device layer. This etching not only separates the devices from the substrate surface but also selectively creates an empty pocket between the two device layers by etching away the sacrificial layer from between.

Figure 2:
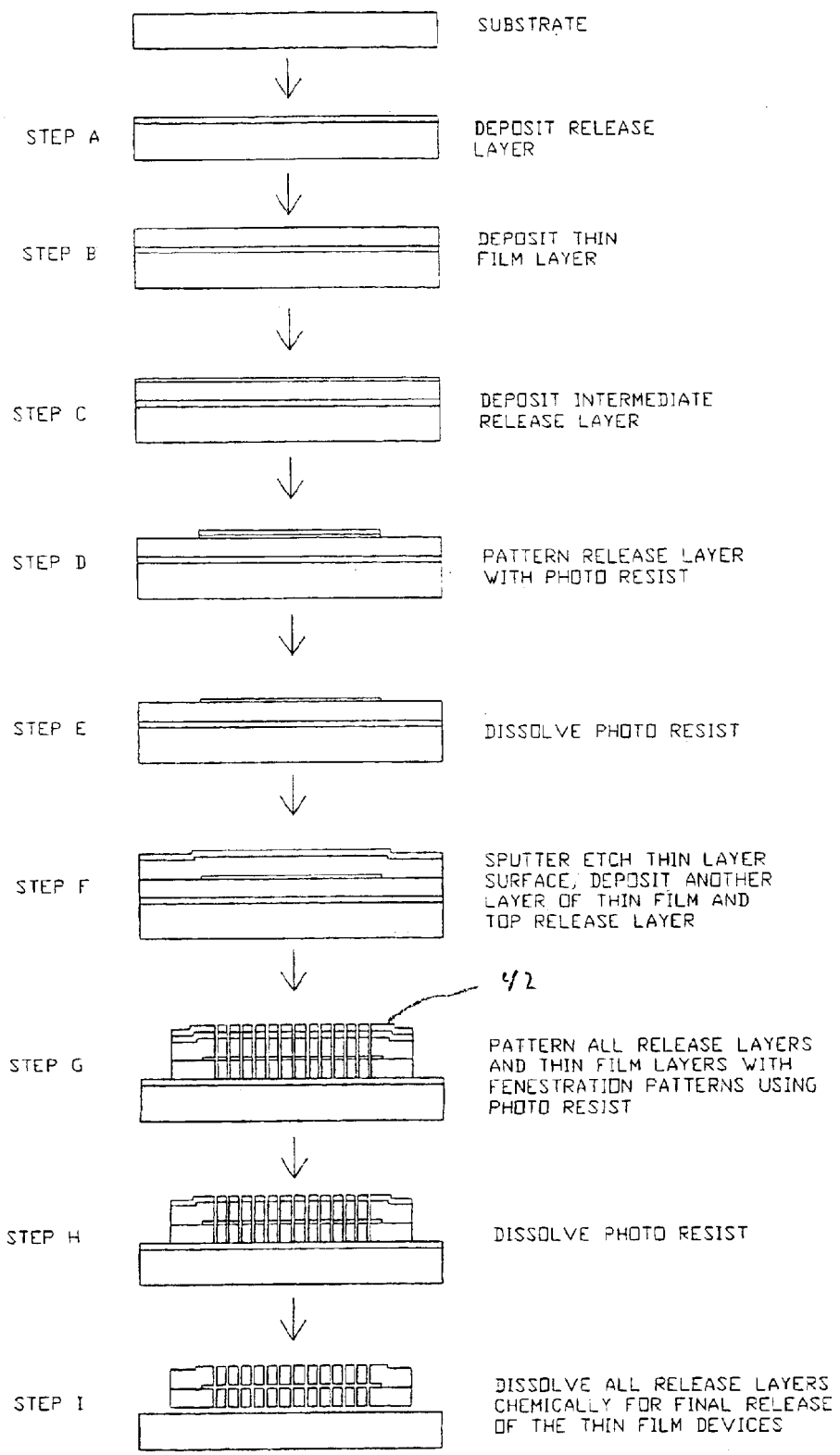
FIG. 2 is a block diagram showing the general steps in the method of another embodiment of the invention.

FIG. 2 shows the principal steps in the method of fabricating two-layered thin film devices having fenestration patterns etched into the thin film. To create fenestration patterns, the photo resist layer 42 in FIG. 2, step G is patterned using mask B which contains the necessary fenestration patterns. The basic process sequence to fabricate thin film devices with fenestration patterns is similar to that described in connection with FIG. 1, except for the added designs on mask B. After patterning the photo resist layer with fenestrations, sacrificial and device layers are patterned by chemical etching (FIG. 2, step G).

Figure 3:
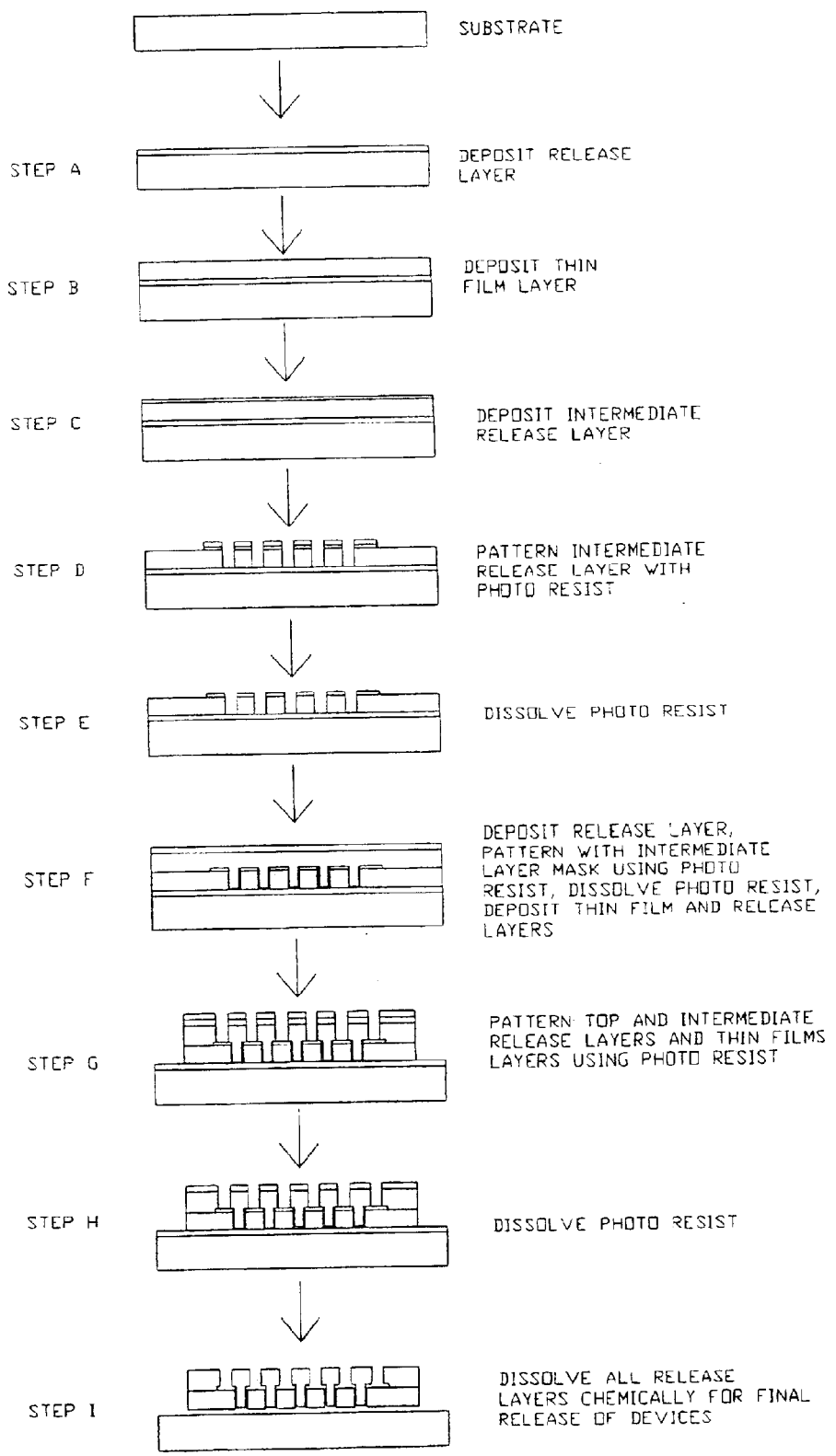
FIG. 3 is a block diagram showing the general steps in the method of another embodiment of the invention.

FIG. 3 illustrates the principal steps in a method of the invention for fabricating two-layered thin film devices with both layers having different fenestration patterns. The designs in mask A and mask B have been modified to fit the new patterns. To create different fenestration patterns in each layer, the photo resist layers as shown in step D and G are patterned using mask plates (mask A and mask B) which contain their own fenestration patterns.

Figure 4:
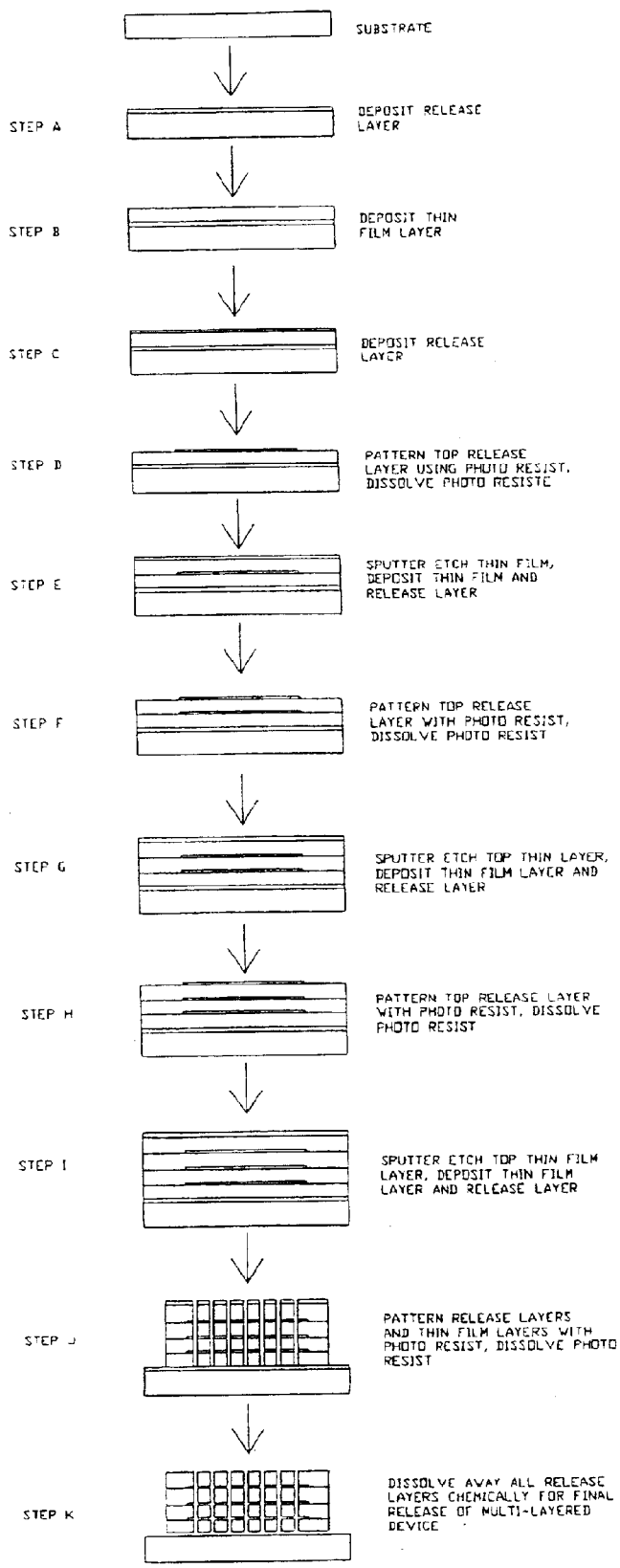
FIG. 4 is a block diagram showing the general steps in the method of another embodiment of the invention.

FIG. 4 illustrates the principal steps in the method of fabricating thin film devices with more than two device layers. The multiple sputtered layers of sacrificial and device materials are added sequentially. The figure shows an example in which the method fabricates a device with four device layers. Such devices may be fabricated with or without fenestration patterns. Following the method of FIGS. 1 and 2, additional layers of sacrificial and device material can be repeatedly sputter deposited and patterned. The number of required mask plates increases proportionally with the number of layers to be patterned. The process sequence to fabricate devices with four device layers of sputtered thin film is illustrated in FIG. 4.

The released multi-layered thin film devices from the steps of the methods in FIGS. 1–4 are in planar form which may be of various geometric shapes such as triangular, rectangular, semicircular and the like as required by the particular application. These multi-layered thin film shapes are then transformed into their corresponding three-dimensional shapes by inserting a suitable stainless steel mandrel (not shown) into the pockets between the layers and re-annealing them at 500° C. in vacuum. The mandrel is made in a size and shape which is commensurate with the desired three dimensional shape of the end-use device. Re-annealing of the thin film with the mandrel inserted causes the shape-setting according to the shape of the mandrel. In case of the device material being a shape memory alloy, the resulting shape is the memory shape that the SMA layers forcefully revert to when heated through the phase change transformation temperature. In the human body the approximate 98° F. (36.6° C.) blood temperature heats the device through the transformation temperature resulting in it deforming to the conical, cylindrical, hemispherical or other shape which is desired for the particular end-use application.

Figure 5:
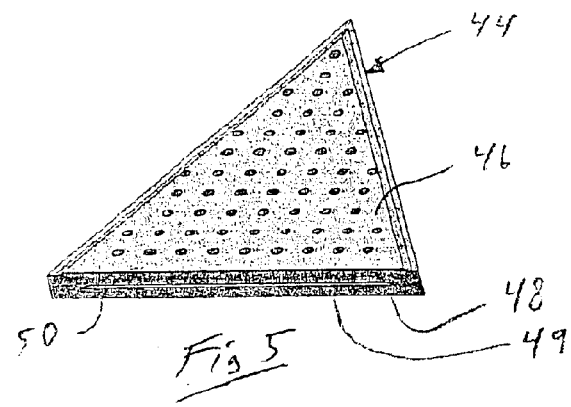
FIG. 5 is a perspective view of a multi-layered thin film triangular planar form before three-dimensional shaping.

FIG. 5 illustrates a triangular multi-layered thin film fenestrated planar form structure 44 made in accordance with one method of the invention. The top layer 46 is joined with bottom layer 48 along the left and right sides as view in the figure, and creating a pocket between these layers everywhere else.

Figure 6A:
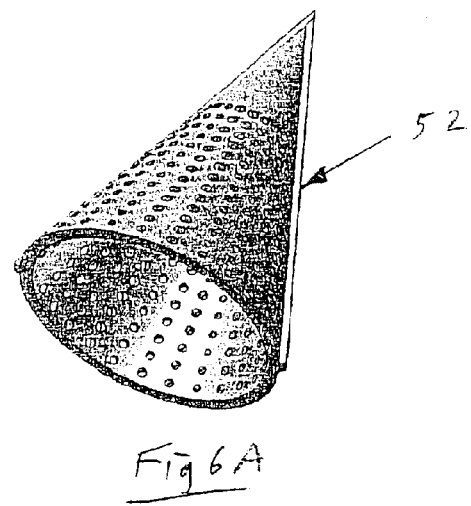
FIG. 6A is a perspective view of a cone made by three-dimensional shaping from the planar form of FIG. 5.

FIG. 6A illustrates a thin film conical shell device 52 made after three-dimensional shaping from the planar form of FIG. 5. The shaping step is carried out by inserting a conformable cone shaped mandrel, not shown, into opening 49 of the planar form, and by heat-treating at 500° C. in vacuum with the mandrel placed inside.

Figure 6B:
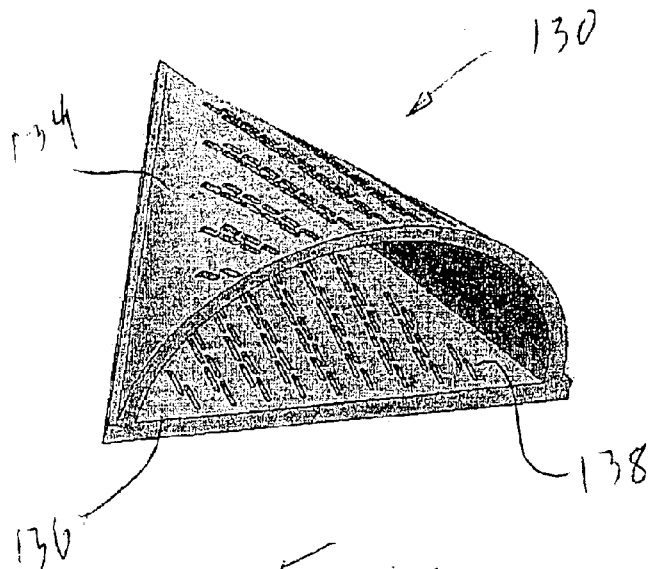
FIG. 6B is a perspective view of a half-conical shell device in accordance with another embodiment.

FIG. 6B illustrates a thin film half-conical shell device 130 made after three-dimensional shaping from a planar form of FIG. 5. The device is formed by deforming one layer 134 into a conical shape while the other layer 136 remains flat. A pattern of fenestrations 138 is formed in each layer.

Figure 7:
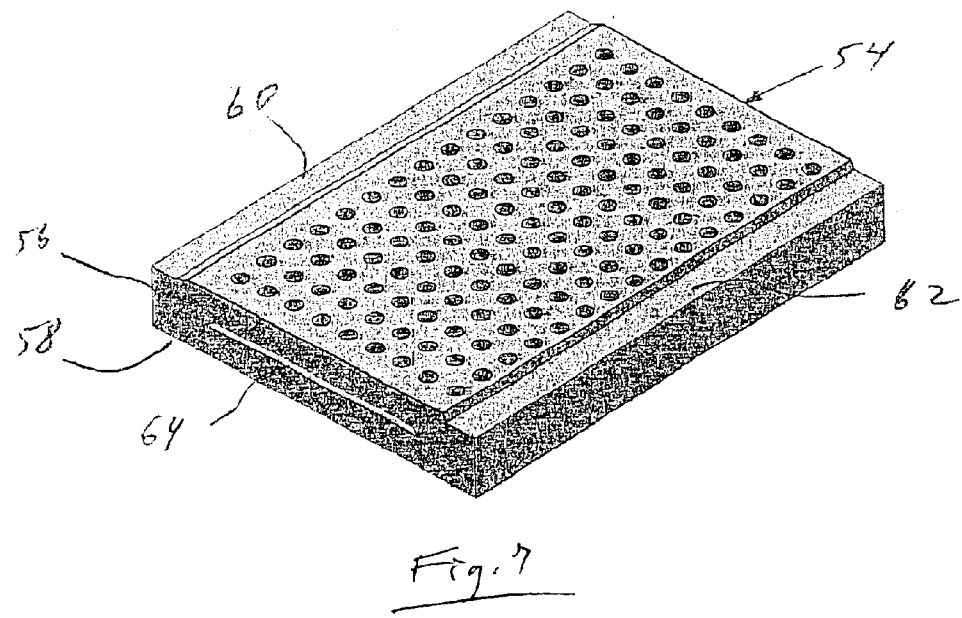
FIG. 7 is a perspective view of a multi-layered thin film rectangular planar form before three-dimensional shaping.

FIG. 7 illustrates a rectangular multi-layered thin film planar fenestrated form structure 54 made in accordance with one method of the invention. The top and bottom layers 56 and 58 of the structure are joined along two opposing sides 60 and 62, and spaced apart to form openings 64 everywhere else.

Figure 8B:
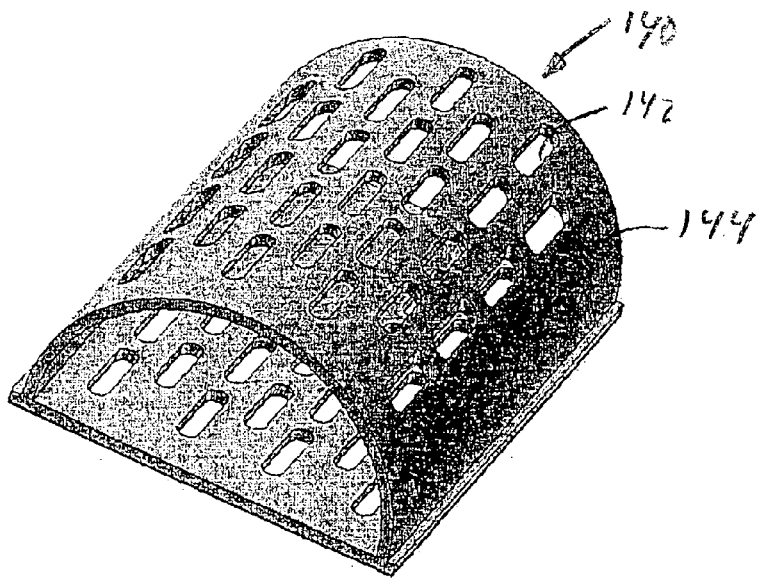
FIG. 8B illustrates illustrates a thin film half-cylindrical shell device in accordance with another embodiment.
Figure 8A:
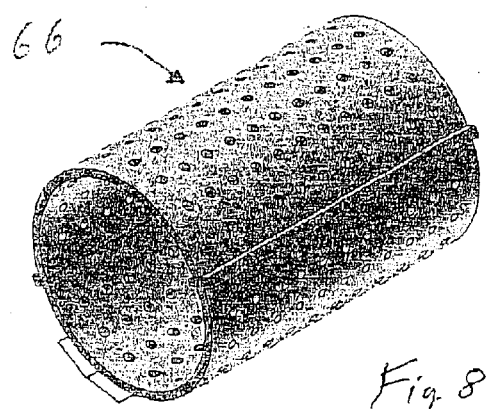
FIG. 8A is a perspective view of a cylinder made by three-dimensional shaping from the planar form of FIG. 7.

FIG. 8A illustrates a thin film cylindrical shell device 66 made after three-dimensional shaping from the planar form of FIG. 7 using a cylindrical shaped mandrel.

FIG. 8B illustrates a thin film half-cylindrical shell device 140 made by three-dimensional shaping from the planar form of FIG. 7. A pattern of fenestrations 142 are formed in each layer. One layer 144 is deformed into a cylindrical shape while the other layer 146 remains flat.

Figure 9:
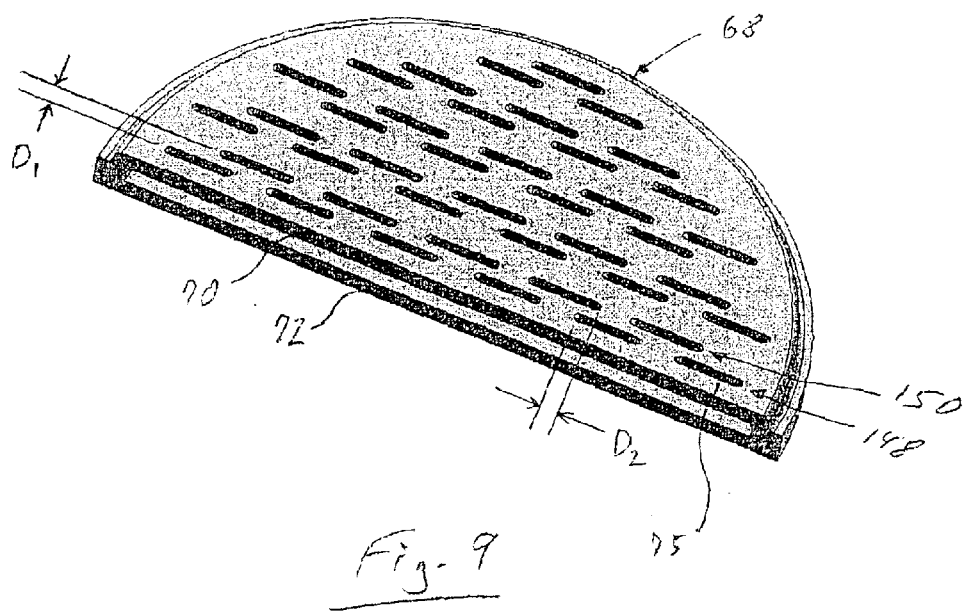
FIG. 9 is a perspective view of a multi-layered thin film semicircular planar form before three-dimensional shaping.

FIG. 9 illustrates a semi-circular shaped multi-layered thin film planar form structure 68 made in accordance with one method of the invention. The top and bottom layers 70 and 72 are joined along the curved sides, and are spaced apart to form an opening 74 everywhere else. A pattern of fenestrations 75 are formed in each layer.

Fenestrations 75 are specifically shaped as slots and positioned to enable the thin film layers to transform from a planar shape into a spherical or spheroidal (meaning the type of shape made by rotating an imaginary curved line, such as an ellipse, about an axis) shape. The specific shape and placement of the slots in device 84 is critical because if an unfenestrated layer of a metal or metal alloy material were to be deformed into a spherical or spheroid shell then portions of the layer would be stretched beyond the material's elastic limit and tear. In the invention, the specific shape and positioning of slots 75 is made by forming them in a plurality of transversely spaced apart rows 148, 150. The slots in each row are laterally offset a distance $D_1$ from the slots in the rows adjacent to it. The slots in each row are also longitudinally spaced-apart a distance $D_2$. The distances $D_1$ and $D_2$ are selected, depending on factors such as thickness and type of material, to be sufficient to enable deformation of the layer into the three dimensionally curved shape. This is because the layer portions joining the slots are only stretched below the material's elastic limit, while the lateral stretching between the slots in all the rows in combination is sufficient to enable deformation into a spherical or spheroidal shape.

Figure 10:
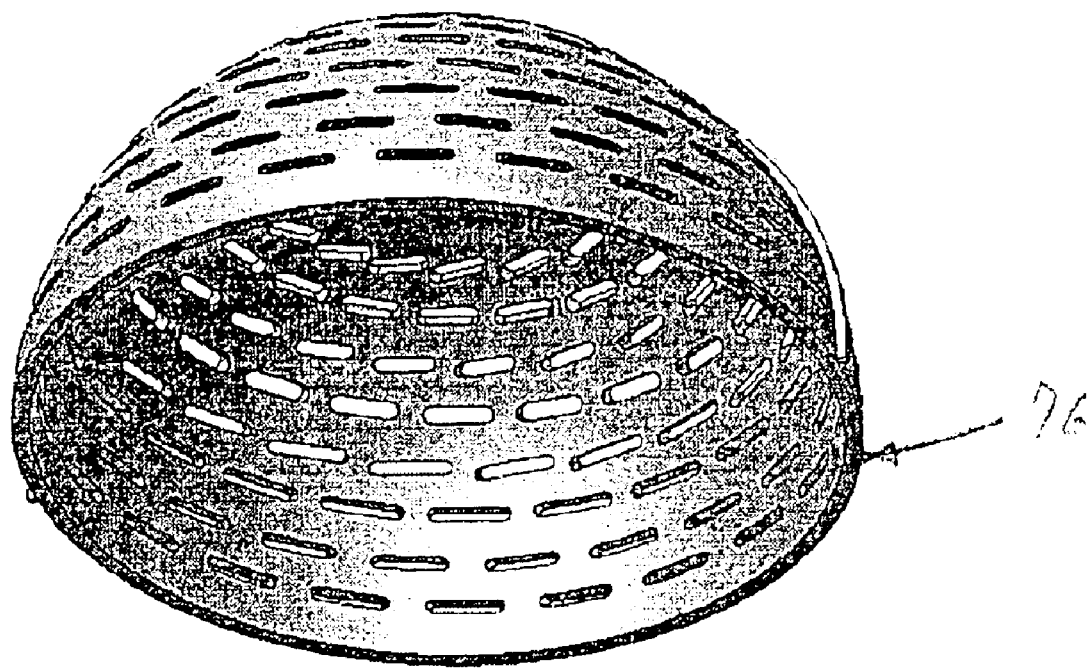
FIG. 10 is a perspective view of a hemisphere made by three-dimensional shaping from the planar form of FIG. 9.

FIG. 10 illustrates a thin film hemispherical shell device 76 made after three-dimensional shaping from the planar form of FIG. 9 using a hemispherical shaped mandrel.

Figure 11:
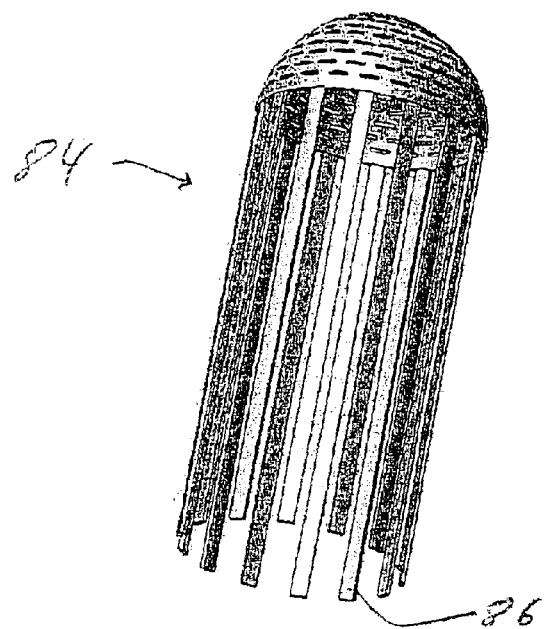
FIG. 11 is a perspective view of a three dimensional hemispherical shell device in accordance with another embodiment.

FIG. 11 illustrates a superelastic hemispherical SMA thin film fenestrated device 84 made with a plurality of narrow strings 86. The strings are formed integral with and in circumferential spaced relationship about the rim of the hemisphere and extend parallel with the longitudinal axis of the device. Suitable dimensions for the hemisphere are a diametrical size on the order of 1 mm to tens of millimeters with the strings each having a width in the range of 50 microns to few millimeters and a film thickness in the range of 1 mm to 50 mm.

In this embodiment, the strings are made by fabricating a thin film cylindrical shell extending from the hemisphere's rim (all one material). Then parallel, longitudinal extending strings are formed by the photolithography and etching processes. The fenestration pattern in the thin film hemisphere is such that it allows to deform into a hemisphere. The thin film device is superelastic at body temperature.

Figure 12:
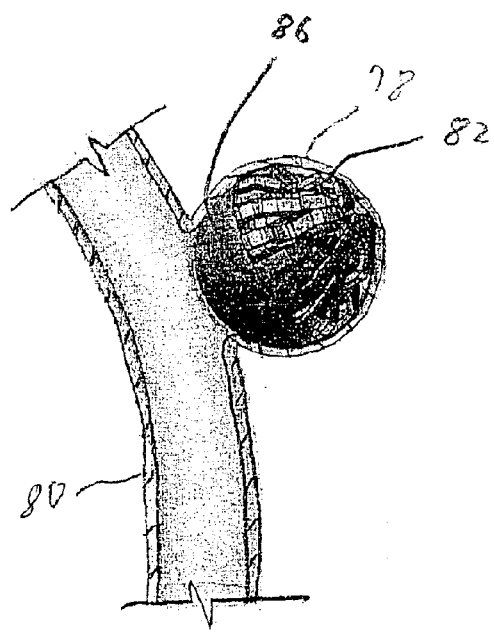
FIG. 12 is a partially cut-away perspective view showing the insertion of the hemispherical shell of FIG. 11 into an aneurysm of the human body.

FIG. 12 illustrates placement of the hemispherical thin film device 86 of FIG. 11 within an aneurysm 78 in a manner which covers the neck opening in the blood vessel 80 from which the aneurysm has erupted. The thin film device is initially folded and inserted (called loading of the device) into a microcatheter at the room temperature. The tubing of the microcatheter prevents the device from opening and the device opens only when the device is pushed out of the microcatheter at body temperature. For this application, the thin film hemispherical device can be made from a shape memory alloy such as nitinol. The superelastic property enables the device to deform as they are guided through the endoluminal spaces and into the aneurysm by suitable means, such as a microcatheter. When deployed in an aneurysm, the device warms up to the blood temperature and actuates from its folded shape to its original ÒmemoryÓ hemispherical shape. The strings simply fill the aneurysm volume and keep the hemispherical device in its position. The stagnant blood inside the aneurysm volume causes the formation of a thrombosis. The resulting thromboembolism in the aneurysm and the presence of the hemispherical thin film device at the neck of the aneurysm block further intrusion of blood into the aneurysm. This results in protection against a life-threatening build up of blood pressure and possible eventual rupture of the aneurysm wall.

When initially inserted endolumenally into the human body, the strings or tentacles of the hemispherical device are below their transition temperature in their cold state. In this state they are sufficiently plastic to enable them to be folded, loaded into a microcatheter, dragged through small and sinuous blood vessels in the brain or other part of the body, and deployed in an aneurysm in the manner shown in FIG. 11. When heated by the blood to the transition temperature, the strings have sufficient strength to tangle together but, because of their small size, insufficient strength to straighten out from shape memory recovery so that they do not rupture the wall of the aneurysm. The tangled strings will fill the aneurysm volume and accelerate formation of a thrombus within the void. This will stop blood flow into the aneurysm to prevent a rupture of the aneurysm and ultimately a stroke.

Figure 13:
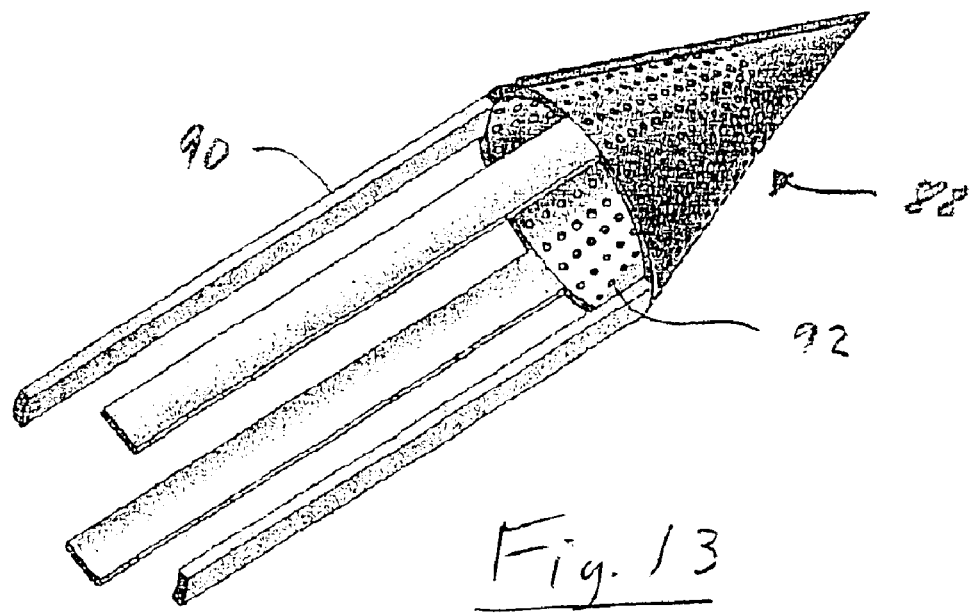
FIG. 13 is a perspective view of a cone device with integral strings or tentacles in accordance with another embodiment.

As shown in FIG. 13 for another embodiment, a conical thin film SMA device 88 with integral strings 90 is fabricated using the foregoing processes. Device 88 is formed with fenestrations 92 for use as a blood clot retriever device to filter or capture and remove any blood clots in small blood vessels. With the strings this filter device will be folded and loaded into a microcatheter. The microcatheter is then used to drag the folded device through a blood vessel to the site of any blood clot. The device then deploys by unfolding as the SMA recovers to its memory shape responsive to being heated through its transition temperature. The conical basket then captures and removes the clot as the microcatheter is withdrawn.

Figure 14:
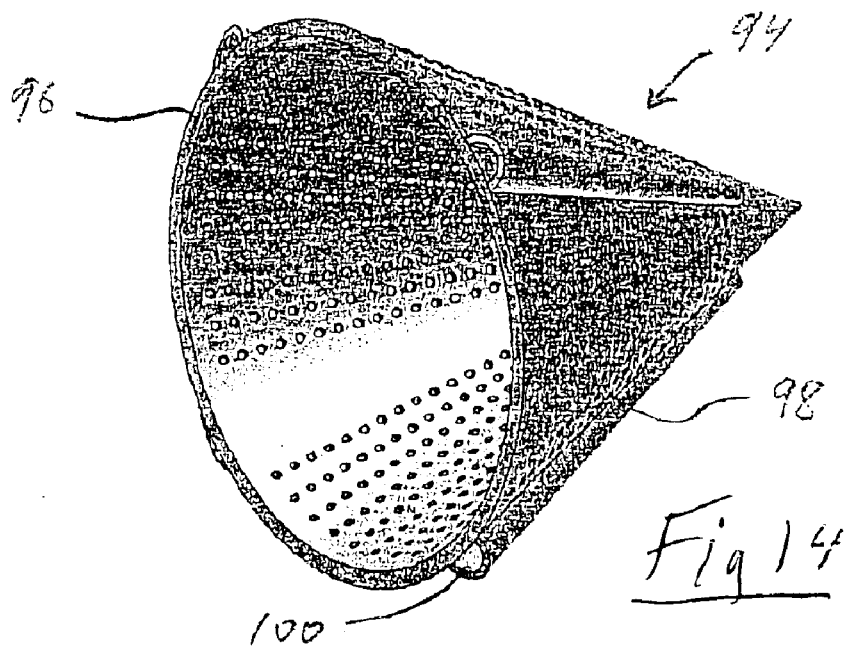
FIG. 14 is a perspective view of a fenestrated conical device shaped with pockets for seating strings in accordance with another embodiment.

FIG. 14 shows an SMA thin film fenestrated structure 94 in accordance with another embodiment comprising a conical shell 96. The shell is fabricated similar to that described in connection with FIGS. 5–6 and further comprises a plurality, shown as four, of pockets 98 position in spaced relationship about the shell's rim. The pockets have openings 100 at the circular rim of the shell. Fabrication method as shown in FIG. 4 is used to fabricate such devices with pockets.

Figure 15:
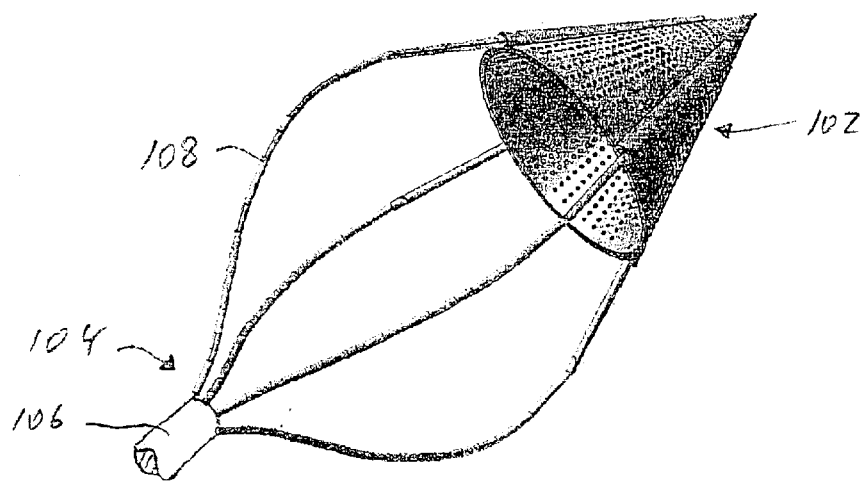
FIG. 15 is a perspective view of the conical device of FIG. 14 with strings seated shaped in the pockets.

FIG. 15 shows another version of a blood clot removal device 102 which is comprised of the fenestrated structure 94 of FIG. 14 together with a cage 104. The cage comprises a strut 106 which is integrally formed with a plurality of elongated thin fingers or wires 108 equal in number to the number of pockets 100 on the shell. The strut and fingers can be formed of any material which is suitable for insertion into and attaching with the pockets, such as SMA, other alloy, metal or polymer. The struts and fingers can be formed from a tube using laser cutting and electropolishing techniques.

Figure 16:
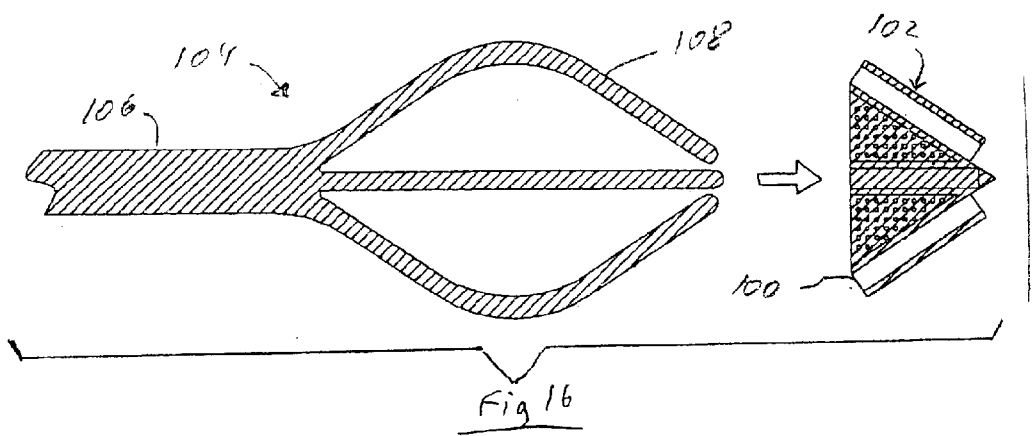
FIG. 16 is a schematic view in cross section showing one step in assembly of the conical device of FIG. 15.
Figure 17:
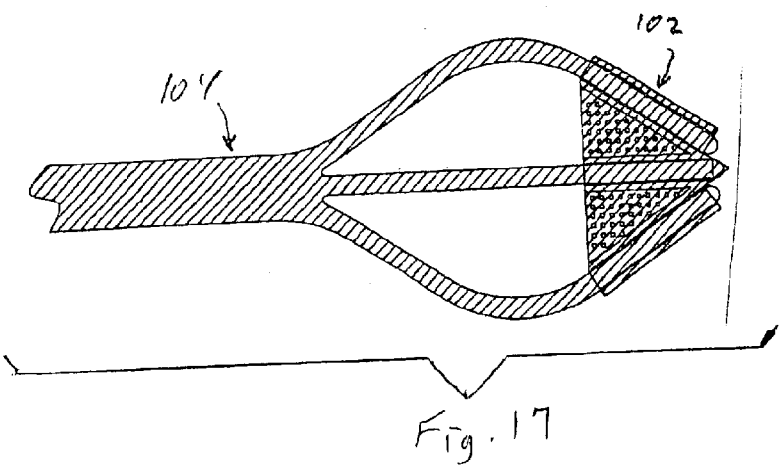
FIG. 17 is a schematic view in cross section showing another step in assembly of the conical device of FIG. 15.

FIG. 16 shows an initial step in assembly of cage 104 with the shell, which is done before inserting device 102 endolumenally into the body. In this stage the finger tips are drawn together. Then each tip is moved radially out into register with its corresponding shell pocket. Then the strut and shell are moved toward each other so that the finger tips are inserted into locking engagement with the pockets in the manner shown in FIG. 17. The strut loaded with the thin film device is then inserted into a microcatheter which can be used to drag the device through a blood vessel for capturing and removing any blood clot in the manner described in connection with FIG. 13. The fenestrations on the device are small enough to allow blood flow through device 102 while preventing passage of any blood clots. As used herein, fenestration means an opening having rectilinear sides such as rectangular, triangular or the like, or having curvilinear sides such as circular, oval or the like.

Figure 18:
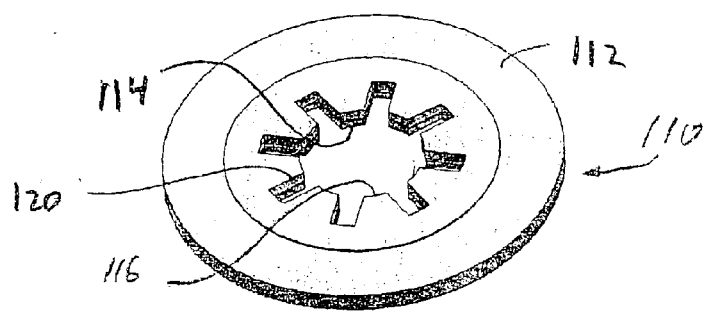
FIG. 18 is a perspective view of a multi-layered thin film circular planar form in accordance with another embodiment.
Figure 19:
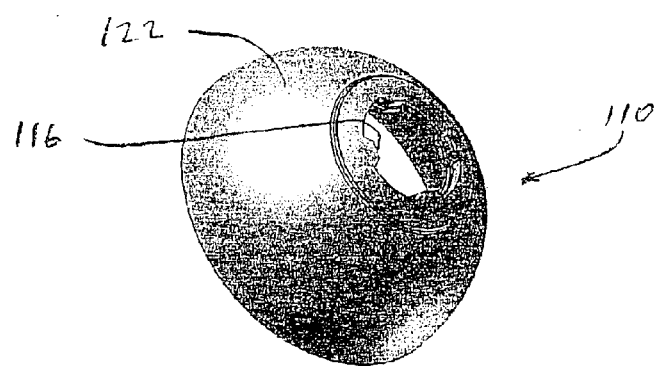
FIG. 19 is a perspective view of a hemispherical ocular device made by three-dimensional shaping from the planar form of FIG. 16.
Figure 20:
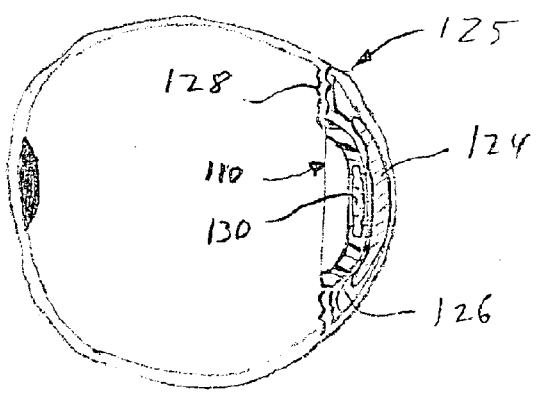
FIG. 20 is a schematic view in longitudinal section a human eye implanted with the device of FIG. 19.

In addition to the fenestration patterns, pockets between the two layers can be created by the use of sacrificial layers as shown. Thus, FIGS. 18–20 show an intraocular device 110 in accordance with another embodiment comprising a thin film structure which provides a means for implanting and anchoring a lens, for example a plastic lens for replacing an incompetent lens, within the human eye. The thin film structure is fabricated by the sputtering methods described herein into a circular flat form having top and bottom layers 112 and 114. During fabrication a window 116 is centrally formed in both layers. The outer peripheral edges of the two layers are joined together. The inner margins of the layers surrounding the window are axially spaced apart to form an inwardly directed circular empty slot 118, best shown in FIG. 21. A plurality of notches 120 are formed in the layers around the window so that the remaining slot material forms pockets into which the lens can be supported. Then the structure is shaped into the hemispherical shell 122 shown in FIG. 19 by the use of a suitable shaping tool, such as a mandrel and heat treatment.

Figure 21:
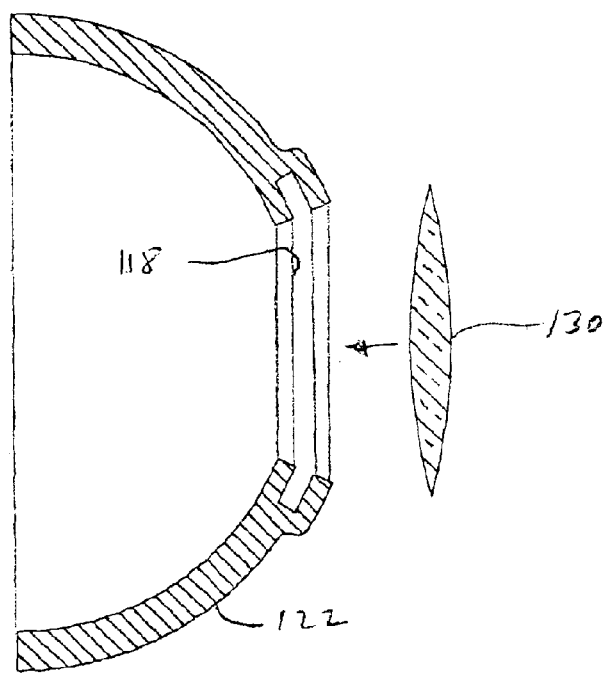
FIG. 21 is a schematic view in cross section showing one step in the fitment of a lens into the ocular device of FIG. 19.
Figure 22:
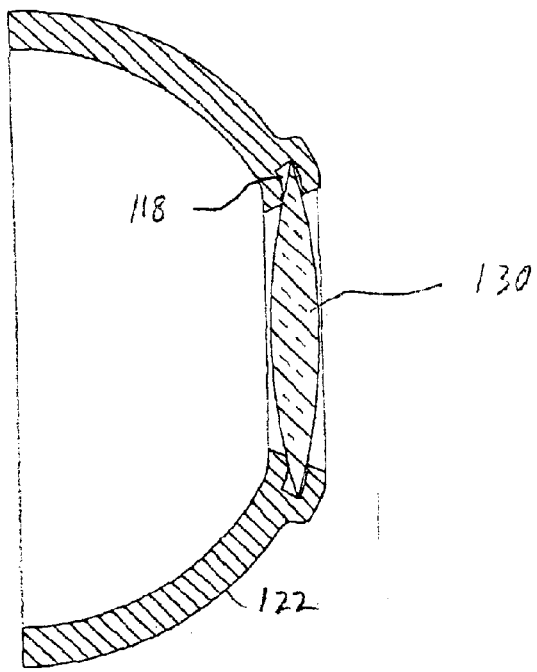
FIG. 22 is a schematic view in cross section showing another step in the fitment of a lens into the ocular device of FIG. 19.

As shown in FIG. 20, device 110 is surgically placed within the eyeball 125 behind the cornea 124 and iris 126. The outer rim of the device is fitted between the ring of muscles 128, which would otherwise be attached to the natural lens for the control of focus accommodation. Then a replacement lens 130 of a plastics or other suitable material, shown prior to its insertion in FIG. 21, is fitted with its outer rim seated within the pockets of slot 118 as shown in FIGS. 20 and 22.

In another embodiment employing the methods herein an anastomosis device can be made by fabricating three thin film cylinders or tubing, not shown, having nearly the same diameter, each of which resembles a stent. To join two blood vessel ends, a short segment of one of the cylinders is compressed and inserted into the lumen of each blood vessel end. This cylinder is then allowed to expand so that the lumen is held open. The two other thin film cylinders are then expanded and slipped over respective ones of the two ends; these two cylinders are permitted to contract radially. Upon completion of the procedure, the two severed blood vessel ends are secured between an internal cylinder that presses outward radially, and external cylinders that gently press inward radially. This method of anastomosis is relatively quick, provides an optimum resistance to collapse, and provides a scaffold for healing.

The methods of fabricating three-dimensional thin film shapes and devices as described may vary according to a specific application. This invention also applies to thin film devices made from materials other than shape memory alloy which can be sputter deposited. While we have described and illustrated the use of this invention in relation to medical device applications, various other devices for other applications may be created using the methods. While various embodiments of the devices and their methods of fabrication have been described, other configurations and embodiments may also be devised within the true spirit and the scope the invention as set forth in the accompanying claims:

What is claimed is:

1. A method of fabricating an article for use in shaping a three dimensional thin film device comprising the steps of providing first and second thin film device layers, the device layers each being formed of a device material selected from the group consisting of a device material which is of the same type of material for both layers, and a device material for the first layer which is of a different type of material from the device material for the second layer, the first and second layers each having first and second portions, joining the first portions of the layers together, providing a sacrificial layer between the second portions, removing the sacrificial layer leaving a space between the second portions, and plastically deforming at least one of the first and second device layers sufficient to change the size of the space.

2. A method as in claim 1 in which the steps of providing the device layers are carried out by depositing a first release layer of a material on a substrate, depositing the first device layer on the first release layer, depositing a second release layer of a material on the first device layer, removing a portion of the second release layer leaving a pattern which comprises an other portion which remains of the second release layer that does not cover the first portion of the first device layer, and depositing the second device layer on the other portion and the first portion of the first device layer.

3. A method as in claim 2 in which the step of joining is carried out by the causing the first portion of the second device layer to join with the first portion of the first device layer during the step of depositing the second device layer.

4. A method as in claim 2 including the step of forming the second release layer of a material selected from the group consisting of Cr, Al, Ag, Au, TiCuAg and TiCuAgCr, polyimide and a photoresist.

5. A method as in claim 1 and further comprising the step of deforming at least one of the device layers in a direction which enlarges the space.

6. A method of fabricating an article for use in shaping a three dimensional thin film device comprising the steps of providing a thin film base layer, providing a thin film second layer, the base and second layers each being formed of a device material selected from the group consisting of a device material which is of the same type of material for both layers, and a device material for the base which is of a different type of material from the device material for the second layer, the base and second layers each having first and second portions, joining the first portions of the layers together, providing a space between the second portions, deforming at least one of the layers into a three dimensional shape, and the step of deforming the one layer is carried out by inserting a mandrel sufficiently far into the space to spread the second portions of the layers apart.

7. A method of fabricating an article for use in shaping a three dimensional thin film device comprising the steps of providing a thin film base layer, providing a thin film second layer, the base and second layers each being formed of a device material selected from the group consisting of a device material which is of the same type of material for both layers, and a device material for the base which is of a different type of material from the device material for the second layer, the base and second layers each having first and second portions, joining the first portions of the layers together, providing a space between the second portions, and the step of deforming the one layer is carried out by inserting a mandrel of a desired shape into the space with a force which is sufficient to deform the one layer into a shape which is commensurate with the desired shape.

8. A method as in claim 1 in which the steps of providing the first and second device layers are carried out by sputter depositing the materials of the device layers.

9. A method as in claim 1 in which the steps of providing the first and second device layers are carried out by forming the device material of a shape memory alloy.

10. A method as in claim 1 and further comprising the step of forming fenestrations in at least one of the first and second device layers.

11. A method of fabricating an article for use in shaping a three dimensional thin film device comprising the steps of providing a thin film base layer, providing a thin film second layer, the base and second layers each being formed of a device material selected from the group consisting of a device material which is of the same type of material for both layers, and a device material for the base which is of a different type of material form the device material for the second layer, the base and second layers each having first and second portions, joining the first portions of the layers together, providing a space between the second portions, the steps of providing the base and second layers are carried out by depositing a first release layer of a material on a substrate, depositing the base layer on the first release layer, depositing a second release layer of a material on the base layer, removing a portion of the second release layer leaving a pattern which comprises another portion which remains of the second release layer that does not cover the first portion of the base layer, depositing the second base layer on the other portion and the first portion of the base layer, depositing a third release layer on the second base layer, removing a first portion of the third release layer leaving an other pattern comprising a second portion that remains of the third release layer, and depositing a third base layer of the device material on the first and second portions of the third release layer while causing a portion of the second base layer of the device material to join with a portion of the third base layer of device material which is not covered by the second portion of the third release layer.

12. A method as in claim 1 comprising the steps of forming the first and second device layers into a planar form structure having a shape selected from the group consisting of polygonal and curvilinear.

13. A method as in claim 12 which the polygonal shape is selected from the group consisting of triangular and rectangular.

14. A method as in claim 12 which the curvilinear shape is selected from the group consisting of semicircular and circular.

15. A method of fabricating an article for use in shaping a three dimensional thin film device comprising the steps of providing a thin film base layer, providing a thin film second layer, the base and second layers each being formed of a device material selected from the group consisting of a device material which is of the same type of material for both layers, and a device material for the base which is of a different type of material from the device material for the second layer, the base and second layers each having first and second portions, joining the first portions of the layers together, providing a space between the second portions, forming a plurality of fenestrations through at least one layer while positioning the fenestrations in a plurality of transversely spaced apart rows and with the fenestrations in each row being longitudinally spaced a first distance apart and further with the fenestrations in one row being longitudinal offset a second distance from the fenestrations in the rows adjacent to the one row, the first and second distances being sufficient to enable deformation of the one layer into a three dimensionally curved shape.

16. A method as in claim 15 and further including the step of deforming the one layer into a three dimensionally curved shape.

17. A method as in claim 16 and in which the deforming step is carried out by deforming the one layer into at least a portion of a shape selected from the group consisting of a sphere and a spheroid.

18. A method as in claim 15 in which the forming step is carried out by forming the fenestrations into slot shapes.

19. A method of fabricating an article for use in shaping a three dimensional thin film device comprising the steps of providing first and second thin film device layers, the device layers each being formed of a device material selected from the group consisting of a device material which is of the same type of material for both layers, and a device material for the first layer which is of a different type of material from the device material for the second layer, the first and second layers each having first and second portions, joining the first portions of the layers together, providing a sacrificial layer between the second portions, and removing the sacrificial layer leaving a space between the second portions, providing the device material of at least one of the device layers to be a shape memory alloy, deforming the one device layer into a three-dimensional shape, and heating the one device layer at a temperature and time which are sufficient to cause the shape memory alloy to anneal while causing shape-setting of the one device layer into a memory shape which is commensurate with the three-dimensional shape.

20. A method as in claim 6 and further comprising the steps of providing the device material of the one device layer to be a shape memory alloy, and heating the one device layer at a temperature and time which are sufficient to cause the shape memory alloy to anneal while causing shape-setting of the one device layer into a memory shape which is commensurate with the three-dimensional shape.

21. A method as in claim 7 and further comprising the steps of providing the device material of the one device layer to be a shape memory alloy, and heating the one device layer at a temperature and time which are sufficient to cause the shape memory alloy to anneal while causing shape-setting of the one device layer into a memory shape which is commensurate with the three-dimensional shape.

* * * * *